United States Patent [19]

Ali et al.

[11] Patent Number: 4,481,193

[45] Date of Patent: Nov. 6, 1984

[54] DES-PROLINE VASOPRESSIN ANTAGONISTS

[75] Inventors: Fadia E. Ali, Cherry Hill, N.J.; William F. Huffman, Malvern, Pa.

[73] Assignee: SmithKline Beckman Corporation, Philadelphia, Pa.

[21] Appl. No.: 586,933

[22] Filed: Mar. 7, 1984

[51] Int. Cl.³ .................... A61K 37/00; C07C 103/52
[52] U.S. Cl. .............................. 424/177; 260/112.5 R
[58] Field of Search ................. 424/177; 260/112.5 R

[56] References Cited

U.S. PATENT DOCUMENTS 4,367,225  1/1983  Manning et al. .................... 424/177
4,399,125  8/1983  Manning et al. .................... 424/177

Primary Examiner—Delbert R. Phillips
Attorney, Agent, or Firm—William H. Edgerton; Richard D. Foggio; Alan D. Lourie

[57] ABSTRACT

Certain octapeptides, which have structures characterized by being a six unit cyclic peptide ring with a dipeptide tail with no proline unit, have vasopressin antagonist activity. An important species of the group is [1-($\beta$-mercapto-$\beta$,$\beta$-cyclopentamethylenepropionic acid)-2-(O-ethyl-D-tyrosine)-4-valine]-7-desproline-8-arginine-vasopressin.

15 Claims, No Drawings

DES-PROLINE VASOPRESSIN ANTAGONISTS

This invention relates to cyclic octapeptides which have vasopressin antagonist activity. More specifically, these new chemical compounds have structures which are characterized by the lack of a prolyl unit at position 7 of the 1-Pmp-VSP antagonist structure.

BACKGROUND OF THE INVENTION

M. Manning, W. H. Sawyer and coworkers have published a series of papers describing various [1-(β-mercapto-β,β-cyclopentamethylenepropionic acid)-4-valine]-arginine-vasopressin congeners which have antivasopressin activity. Representative of these are EPA No. 61,356, U.S. Pat. Nos. 4,367,225 and 4,399,125.

All of the Manning compounds have a tripeptide chain attached at unit 6 of the 6-unit dithio ring and are, of course, nonapeptides. The present compounds are distinguished over these by being des-Pro[7] vasopressins with substantial antagonist activity.

Also, a previously filed U.S. application, Ser. No. 467,117, filed Feb. 16, 1983, discloses certain octapeptide vasopressin congeners which have the 9-Gly unit deleted and which have potent VSP antagonist activity.

All of the previously disclosed compounds have structures which have an essential proline-like unit at position 7 of the vasopressin structures. The compounds of this invention have no such unit in their structures and retain VSP antagonist activity.

In the description herein and in the claims, the nomenclature common in the art of peptide and vasopressin chemistry is used. When no configuration is noted, the amino acid unit is in the L, or naturally occuring, form. In certain structural formulas, the thio members of the Pap and Cys units are added for clarity.

Certain of the peptide art designations used herein are the following: Pap, β-mercapto-β,β-cyclopolyalkylene-propionic acid; Pmp, β-mercapto-β,β-cyclopentamethylenepropionic acid; Abu, α-aminobutyric acid; Chg, cyclohexylglycine; Cha, cyclohexylalanine; Pba, α-aminophenylbutyric acid; Gln, glutamine; Gly, glycine; Tyr, tyrosine; Phe, phenylalanine; Val, valine; Ile, isoleucine; Nle, norleucine; Leu, leucine; Ala, alanine; Lys, lysine; Arg, arginine; Asn, asparagine; Tos, tosylate; BHA, benzhydrylamine; DIEA, diisopropylethylamine; 4-MeBzl, 4-methylbenzyl; TFA, trifluoroacetic acid; DCC, dicyclohexylcarbodiimide; HBT, 1-hydroxybenzotriazole; ACM, acetamidomethyl.

DESCRIPTION OF THE INVENTION

The des-Pro-VSP compounds of the invention are illustrated by the following structural formula:

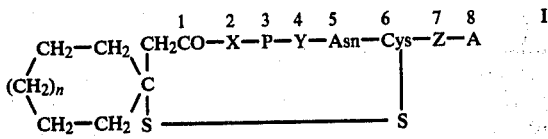

in which:
P is Phe or Phe(4'-Alk);
X is D-Phe, D-Val, D-Nva, D-Leu, D-Ile, D-Pba, D-Nle, D-Cha, D-Abu, D-Met, D-Chg, D or L-Tyr or D or L-Tyr(alk);
Y is Val, Ile, Abu, Ala, Chg, Gln, Lys, Cha, Nle, Phe, Leu or Gly;
Z is D or L-Arg or D or L-Lys;
A is Gly(NH₂), Gly or Gly(NH-Alk); and
n is 0–2, or a pharmaceutically acceptable salt, prodrug ester or complex thereof.

"Alk" in formula 1 and hereafter represents a lower alkyl of 1–4 carbons which is optionally attached either to the nitrogen at A or to the oxygen substituent of the tyrosine unit when the latter is present at position 2. Such alkyl substituents include methyl, ethyl, n-propyl, isopropyl or butyl. Preferably Alk is methyl or ethyl. "Bzl" represents benzyl.

When the term, "vasopressin", is used, it means L-arginine vasopressin (AVP) unless otherwise modified to indicate a D-arginine, D-lysine or L-lysine vasopressin. The AVP derivatives of this invention are preferred. In the compounds represented by formula I, those with structures having A as Gly(NH₂) are also preferred for VSP antagonism.

A subgeneric group of compounds of this invention comprises compounds of formula I in which P is Phe, X is D-Tyr or D-Tyr(Et); X is Val or Abu; A is GlyNH₂; n is 1 and Z is L-Arg or D-Arg.

A preferred compound of this invention is [1-(β-mercapto-β,β-cyclopentamethylene-propionic acid)-2-(O-ethyl-D-tyrosine)-4-valine-7-des-proline-8-arginine]-vasopressin [(Pmp¹-D-Tyr(Et)²-Val⁴-desPro⁷)-AVP].

Also included in this invention are various derivatives of the compounds of formula I such as addition salts, prodrugs in ester or amide form and complexes. The addition salts may be either salts with pharmaceutically acceptable cations such as NH₄⊕, Ca⊕⊕, K⊕ or Na⊕ at the terminal acid group or with a pharmaceutically acceptable salt at a basic center of the peptide (as in the Arg units). The acetate salt forms are especially useful although hydrochloride, hydrobromide and salts with other strong acids are useful. The compounds, also, form inner salts or zwitter ions as when a terminal carboxy group is present. Prodrugs are derivatives of the compounds of formula I which degrade to the parent compound in vivo. The ester prodrug forms are, for example, lower alkyl esters of the acids of formula I which have from 1–8 carbons in the alkyl radical or aralkyl esters such as various benzyl esters. Other latentiated derivatives of the compounds of formula I will be obvious to those skilled in the art. "Complexes" include various solvates such as hydrates or alcoholates or those with supporting resins, such as a Merrifield resin.

The compounds of formula I are prepared by cyclizing a linear octapeptide intermediate of this invention by means of the two mercapto groups located, respectively, at the cysteine unit at position 6 and the β-mercapto-β,β-cyclopolyalkylene-propionic acid unit (Pap) at position 1. The cyclization reaction occurs in the presence of a mild oxidizing agent which, at high dilution, is capable of oxidizing intramolecularly the mercaptan to a disulfide.

For example, oxidation of the following linear octapeptide;

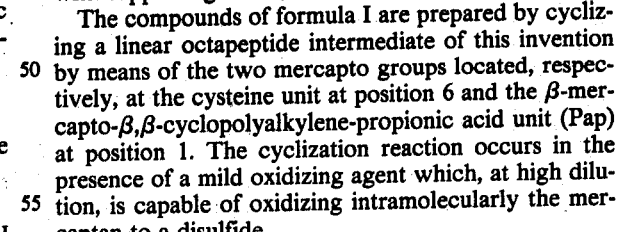

in which P, X, Y, Z, and A are as defined for formula I, but also in which either or both Z and A together are hydrogen, with the mercapto groups (—SH) being members of the Pap and Cys units, is carried out as described generally above. For example, an excess of an alkali metal ferricyanide, such as potassium or sodium ferricyanide, is used, with the linear intermediate dissolved in a suitable unreactive solvent, preferably in an aqueous solvent, at a neutral pH, about 7–7.5, at ambient temperature, or lower, until the reaction is substantially complete. Lower alcohols such as methanol may be added. Preferably, the concentrations of the linear peptide dimercaptan and the oxidizing agent are low, say 0.01 molar concentration of oxidizing agent in several liters of aqueous solution to cyclize 1–5 grams of dimercaptan.

Other mild oxidation agents having an oxidation potential roughly equivalent to ferricyanide may also be used for the ring closure reaction. Oxygen, diiodoethane, or iodine are alternatives. Of course, one skilled in the art will recognize that certain cyclization methods are not appropriate if an interfering reaction site is present in the structure of the starting material of formula II. The linear mercaptan starting material may or may not have protecting groups common to the art present at the various amino acid units or at the mercapto positions. In the former case, the protecting groups are removed after cyclization. In the case of the ACM-SH protecting groups, removal of the protective group and cyclization may both be accomplished using iodine in aqueous methanol. Usually, however, the free linear peptide is cyclized.

The desired cyclic des-proline peptide of formula I is conveniently isolated by acidifying the aqueous oxidation mixture, such as using glacial acetic acid, and passing the reaction mixture over an ion-exchange chromatographic column, for example, over a weakly acid, acrylic resin column with acid elution, or by gel filtration over a bead-formed gel prepared by cross-linking dextran with epichlorohydrin.

In an alternative reaction sequence for preparing the compounds of this invention, the intermediate of formula II in which one or both tail units is missing is cyclized as described above and is then condensed in one or two reactions with the protected amino acid units defined as Z and A for formula I. Reaction conditions for the tail unit attachment are those of any amide producing method known to the peptide art as described above but, particularly, reaction of the tail amino acids whose carboxylic acid group is protected, as described, with the 6-Cys acid in the presence of dicyclohexylcarbodiimide and HBT is used. The protecting groups which may be present on the cyclic Cys acid or the tail units are, then if present, removed to give the products of this invention. Reaction conditions should be selected to minimize racemization of the Cys unit as known to the art.

The important intermediates of formula II, in free or protected form are conveniently prepared using solid-phase methods of peptide synthesis as discussed in M. Manning et al., J. Med. Chem. 25 46 (1982). A commercial benzhydrylamine support resin (BHR) is used to prepare the end products of formula I in which A is Gly(NH$_2$) (the glycinamides) and a chloromethyl support resin (CMR) is used to prepare the compounds of formula I in which A is Gly (the glycines).

The peptide chain of the linear peptides of formula II is built up, stepwise, proceeding from unit 8 working toward unit 1. Each unit is properly protected as known in the peptide art and as described below. The sequence of step reactions is conveniently carried out in a Beckman 990B peptide synthesizer without isolation of each intermediate peptide. The details of the procedure are in the working examples presented hereinafter.

The various amino acids, which are consecutively added to the resin supported chain are protected as known to the art. For example, the Boc protecting group is used for an amino group especially at the α-position; benzylthiomethyl, ethylcarbamoyl, adamantyl, t-butyl, acetamidomethyl, trityl or an optionally substituted benzyl, for the mercapto groups at the Pap and Cys units; nitro; carbobenzoxy, methylene-2-sulfonyl or tosyl for the Arg unit; and ethyloxycarbonyl or an optionally substituted carbobenzoxy(Z) for the Tyr or Lys units. The protective groups should, most conveniently, be those which are easily removed, that is, using acid treatment for the tert.-butyloxycarbonyl (Boc) group, sodium-liquid ammonia or modified catalytic hydrogenation for the benzyl or carbobenzoxy groups.

The protected linear peptide intermediate is split from the carrying resin matrix, for example, by using ammonia in an aqueous miscible solvent, and, then, is treated to remove the protective groups, such as by using sodium-liquid ammonia. This procedure gives the amide derivative of the linear octapeptide.

More conveniently, the two steps are combined by treating the resin supported peptide with anhydrous hydrogen fluoride using a suitable carbonium ion scavenger, such as anisole, to give the des-proline peptide intermediate of formula II in good yield.

The compounds of this invention have potent vasopressin antagonist activity. Vasopressin is known to contribute to the anti-diuretic mechanism of action within the kidney. When the action of these compounds antagonizes that of the natural anti-diuretic hormone (ADH), the body excretes water due to an increased permeability of the terminal portions of the renal tubule. We believe the mechanism of action is at the vasopressin receptors (V$_2$-receptors) located on the plasma membrane of certain renal epithelial cells. The most notable pharmocodynamic effect of the ADH antagonists of the invention is that of a water diuretic rather than of a natriuretic such as a thiazide.

Any patient suffering from the syndrome of inappropriate antidiuretic hormone secretion (SIADH) or from an undesirable edematous condition is a target for the claimed compounds. Examples of clinical conditions indicated for the compounds of this invention include hypertension, hepatic cirrhosis, congestive heart failure or a component of any traumatic condition resulting from serious injury or disease.

The second group of vasopressin receptor sites are the vascular pressor sites (V$_1$-receptors) within the cardiovascular system itself. These may also be somewhat antagonized by the compounds of this invention resulting in anti-hypertensive activity. Dysmenorrhea is another utility for the compounds of this invention when administered intravenously or intranasally.

The compounds of this invention, therefore, are used to treat edema or to expell water in patients in need of such treatment by administering internally, particularly parenterally or by insufflation, a nontoxic but effective quantity of the chosen compound, preferably combined with a pharmaceutical carrier. Dosage units of the active ingredient are selected from the range 0.05 to 20 mg/kg, preferably 1 to 5 mg/kg, based on a 70 kg patient. The dosage units are administered from 1 to 5 times daily.

The pharmaceutical composition which contains an active ingredient of formula I comprises a dosage unit as described above dissolved or suspended in a standard liquid carrier, such as isotonic saline, contained in an ampoule or a multiple dose vial suitable for a parenteral injection such as for intravenous, subcutaneous or intramuscular administration. A compound for insufflation may be similar but is usually administered in a metered dose applicator or inhaler. Pulverized powder compositions may, also, be used along with oily preparations, gels, buffers for isotonic preparations, emulsions or aerosols.

Antagonistic activity toward the natural antidiuretic hormone (anti-ADH activity) is determined, in vitro, in the medullary tissue of hog or human kidneys and, in vivo, in the hydropenic rat. The in vitro assay procedures for vasopressin stimulated adenylate cyclase activation or vasopression binding activity are described by F. Stassen et al., J. Pharmacology and Experimental Therapeutics, 223, 50–54 (1982).

In the test procedure for assay of adenylate cyclase activity, the amount of $^{32}P/cAMP$ formed in the absence of medullary membrane is determined (blank). The blank value is substracted from all experimental data. The compound is tested for its effect on basal adenylate cyclase activity and/or on vasopressin stimulated activity. Each determination is carried out in triplicate. The Ka value is derived from a Lineweaver-Burke plot. Rel. $V_{max}=(V_{max}drug/V_{max}$ vasopressin$)\times 100$. $K_i=I/[Ka'/Ka)-1]$ where I is the concentration of the antagonist, and Ka' and Ka are the concentrations of vasopressin required to give half-maximal activity of adenylate cyclase in the presence and absence of antagonist, respectively.

In the test procedure for binding assays, the amount of $^3H$-vasopressin bound in the absence and in the presence of an excess of vasopressin ($7.5\times 10^{-6}M$) is measured in triplicate. These values represent total and non-specific binding, respectively. The $K_B$ of a compound is derived from the equation for competitive inhibition: $K_B-IC_{50}/(1+L/K_D)$, where $IC_{50}$ is the concentration required for 50% inhibition of $^3H$-vasopressin ($K_D=3.6\times 10^{-9}M$; 1 SD$=0.4\times 10^{-9}M$). This is the average $K_D$ value determined on 3 preparations of hog kidney membranes.

The assay for anti-ADH activity is the hydropenic rat protocol is described below:

Hydropenic Rat Screen

Food and water are removed from male rats approximately 18 hours prior to testing. Animals are housed 4 per metabolism cage. At 0 hour, the test compound is administered intraperitoneally to the test group and an equivalent volume of vehicle is administered to both control groups (fasted and non-fasted). Urine volume and osmolality are measured every hour for 4 hours. Test values are recorded as ml of urine excreted (cumulative), mEq/rat electrolyte excreted, mg/rat urea excreted, and osmolality in milli-Osmoles/kg $H_2O$. A tolerance test is used to determine significance. $ED_{300}$ is defined as the dose of compound (μg/kg) required to lower urine osmolality to 300 m-Osmoles/kg.

TABLE 1

| Compound | Anti-ADH Activity | | | |
|---|---|---|---|---|
| | In Vivo (Rat) $ED_{300}$ (μg/kg)* | In Vitro (Pig) Ki(nM) | In Vitro (Pig) $K_B$(nM) | In Vitro (Human) Ki |
| A | 22.7* | 2.7 | 17 | $9.8\times 10^{-9}M$ |
| B | 11.0* | 9.8 | 13 | $5.7\times 10^{-9}M$ |

(A) [1-(β-mercapto-β,β-cyclopentamethylenepropionic acid)-2-(O—ethyl-D-tyrosine)-4-valine-7-desproline-8-arginine]-vasopressin
(B) [β-mercapto-β,β-cyclopentamethylenepropionic acid)-2-(O—ethyl-D-tyrosine)-4-valine-8-arginine]-vasopressin
*Estimated dose of peptide delivered ip stat (μg/kg) which results in a reduction of $U_{osm}$ from hydropenic levels to 300 m-Osmoles/kg $H_2O$.

The following examples are intended solely to teach the preparation of the compounds of this invention. All temperatures are in degrees Centigrade.

EXAMPLE 1

Solid Phase Synthesis of PmP(4-MeBzl)-D-Tyr(Et)-Phe-Val-Asn-Cys(4-MeBzl)-Arg(Tos)-Gly-BHA Resin For the solid-phase synthesis of the titled resin-supported peptide, BOC-Gly-resin (1.19 mmol/g of resin) was used as a starting material. It was prepared by reacting the symmetrical anhydride (Boc-Gly)$_2$O with the benzhydrylamine resin in dimethylformamide for two hours. The benzhydrylamine resin as hydrochloride salt was pretreated as follows:

(1) Suspended in methylene chloride overnight.
(2) Washed with methylene chloride (4 times, 1 min).
(3) Neutralized with 7% diisopropylethylamine (DIEA) in methylene chloride (2 times, 2 min).
(4) Washed with methylene chloride (6 times, 1 min).
(5) Washed with previously dried dimethylformamide (2 times, 1 min).

The symmetrical anhydride, (Boc-Gly)$_2$O, was prepared as follows:

To a solution of Boc-GlyOH (0.35 g, 2 mmol) in 10 ml of methylene chloride was added 1 ml (1 mmol) of dicyclohexylcarbodiimide in methylene chloride (1M solution). The mixture was rocked on a shaker for 10 min, DCU was filtered off and washed 3×1 ml with methylene chloride. The filtrate was concentrated in vacuum (room temp) to a volume of 0.5 ml. It was dissolved in dimethylformamide and added to the resin. After a complete coupling (1–2 hrs), the resin was washed with dimethyl formamide 2×1 min), followed by methylene chloride (4×1 min). A quantitative ninhydrin test and an amino acid analysis were performed to calculate the percent loading on the resin.

The appropriately protected aminoacids were coupled sequentially on to the Boc-Gly-resin using the Beckman peptide synthesizer 990-B. The program used for each coupling, except Boc-Asn and Pmp(4-MeBzl), was as follows:

(1) Washed with $CH_2Cl_2$ (3 times, 1 min).
(2) Prewashed with 50% TFA in $CH_2Cl_2$ (1 time, 1 min)
(3) Deprotection with 50% TFA in $CH_2Cl_2$ (30 min).
(4) Washed with $CH_2Cl_2$ (3 times, 1 min).
(5) Prewashed with 7% DIEA in $CH_2Cl_2$ (1 time, 1 min).
(6) Neutralized with 7% DIEA in $CH_2Cl_2$ (1 time, 10 min).
(7) Washed with $CH_2Cl_2$ (3 times, 1 min).
(8) Protected amino acid (3 mmol) in $CH_2Cl_2$, followed by addition of DCC, 3 mmol, 10 ml of 0.3M in $CH_2Cl_2$, and coupling for two hours.
(9) Washed with $CH_2Cl_2$ (3 times, 1 min).

(10) Washed with EtOH/CH₂Cl₂ 1:1 (3 times, 1 min).
(11) Washed with CH₂Cl₂ (3 times, 1 min).

In the case of coupling of Asn moiety, 1-hydroxybenzotriazole (HOBT, 6 mmol) was used, 10 ml of 0.6M in dimethylformamide. Dry dimethylformamide was also used as solvent when Pmp(4-MeBzl) was coupled onto the peptide resin, using 4-dimethylaminopyridine (3 mmol). Completion of each coupling reaction was monitored by the ninhydrin test. The 4-methylbenzyl group (4-MeBzl) was used to protect the thiol group of Cys and the pentamethylene-β-mercaptopropionic acid (Pmp) moieties.

The resulting protected peptide resin intermediate i.e. [Pmp(4-MeBzl)-D-Tyr(Et)-Phe-Val-Asn-Cys(4-MeBzl)Arg-(Tos)-Gly-BHA-resin], was washed well with the methylene chloride and dried in vacuo overnight to give 2.0 g of the titled product. This procedure is also used to prepare other resin supported, linear, octapeptide dimercaptans.

EXAMPLE 2

Preparation of

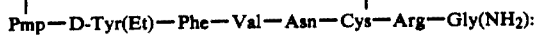
Pmp—D-Tyr(Et)—Phe—Val—Asn—Cys—Arg—Gly(NH₂):

Pmp(4-MeBzl)-D-Tyr-(Et)-Phe-Val-Asn-Cys(4-MeBzl)Arg(Tos)-Gly-BHA-resin, 2.0 g, in 2.5 ml of anisole, was reacted with anhydrous hydrofluoric acid (40 ml) at 0° for 50 minutes. After evaporation in vacuo to dryness, the residue was treated with anhydrous ether and the crude peptide was extracted with degassed dimethylformamide (50 ml) and 33% acetic acid (50 ml) into 4 liters of water. The aqueous diluted disulfhydril octapeptide was cyclized using 0.01M potassium ferricyanide solution at pH 7.2 until color persisted for 30 minutes. After the completion of the oxidation reaction, the pH of the solution was adjusted to pH 4.5 by adding glacial acetic acid. This solution was passed through a weakly acid acrylic resin (Bio-Rex 70) column (2.5×12 cm) slowly. The column was eluted with pyridine-acetate buffer (30:4:66, pyridine/acetic acid/water v/v). The pyridine acetate solution was removed by distillation in vacuo, and the residue was lyophilized from 1% acetic acid to give 420 mg (40%) of crude peptide as titled.

Purification of

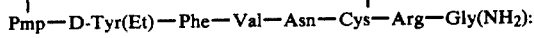
Pmp—D-Tyr(Et)—Phe—Val—Asn—Cys—Arg—Gly(NH₂):

(1) Counter-current distribution (CCD): Sample: 250 mg, n-BuOH:HOAc:H₂O (4:1:5), 240 transfers.
  (a) Fr. 167–189; 83 mg
  (b) Fr. 160–166 and 190–196; 14 mg
(2) Preparative HPLC:
  Sample: 50 mg (from 1a), Altex ODS, 10 mm×25 cm 5u, flow rate 4 ml/min, water/acetonitrile/TFA (60:40:0.25); isocratic, 220 nm (2.0 AUFS), injection 6.25 mg/0.5 ml, 24.3 mg pure sample isolated.
Physical Data:
Molecular Formula: $C_{48}H_{70}N_{12}O_{10}S_2$
Molecular Weight: 1038.46

Amino Acid Analysis: Asp (1.00), Gly (1.00), Cys (0.56), Val (0.96), Tyr (0.70), Phe (0.96), and Arg (0.96).
Chromatography Data:

| Solvent | | RF |
|---|---|---|
| TLC | Butanol:Acetic Acid:Water:Ethyl Acetate (1:1:1:1) | 0.64 |
| | Butanol:Acetic Acid:Water:Pyridine (15:3:3:10) | 0.55 |
| HPLC | C-18 column | K' |
| | isocratic, Water:Acetonitrile:TFA (60:40:0.25) | 4.29 |
| | Gradient, Water:Acetonitrile:TFA (80:20:0.25 to 50:50:0.25), hold for 10' then return to initial condition. | 6.9 |

Fast Atom Bombardment "FAB": $(M+H)^+$ at 1039

EXAMPLE 3

Preparation of

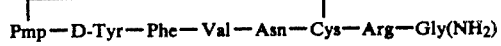
Pmp—D-Tyr—Phe—Val—Asn—Cys—Arg—Gly(NH₂)

PmP(4-MeBzl)-D-Tyr(Br-Z)-Phe-Val-Asn-Cys(4-MeBzl)-Arg(Tos)-Gly-Resin (4.2 g, 1.5 mM), prepared by the method from Example 1, in 4.5 ml distilled anisole, is treated with anhydrous hydrogen fluoride (40 ml) at 0° for one hour. After evaporation in vacuo to dryness, the residue is treated with anhydrous ether and extracted to give 1.33 g of crude peptide. The resulting unprotected octapeptide is cyclized using 0.01M potassium ferricyanide solution at pH 7-7.5 until color persisted for 30 minutes again as described above in Example 2. The titled compound is isolated and purified as described above.

EXAMPLE 4

Preparation of

Pmp—D-Tyr(Et)—Phe—Val—Asn—Cys—Arg—Gly(NHC₃H₇)

A mixture of 0.1 mmole of (Pmp¹-D-Tyr(Et)²-Val⁴-desPro⁷Gly)AVP, prepared as described above and 0.1 mmole of n-propylamine in 20 ml of dimethylformamide is reacted with 23 mg (0.11 mmole) of DCC and 14 mg (0.11 mmole) of HBT at room temperature for 2 hours. The volatiles are evaporated to give an oily product residue. The product is purified using (1) gel filtration over G-10-Sephadex eluted with 0.2N acetic acid, (2) high pressure liquid chromatography using 0.05% TFA in 39% acetonitrile in water and, again, (3) gel filtration to give the pure peptide of the title.

EXAMPLE 5

Substituting a stoichiometric quantity of Boc-L-Tyr(Et) for Boc-D-Tyr(Et) at the 2 unit of the peptide synthesis of Examples 1 and 2 gives

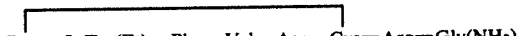
Pmp—L-Tyr(Et)—Phe—Val—Asn—Cys—Arg—Gly(NH₂).

Substituting in Examples 1 and 2, D-Arg(Tos) for L-Arg(Tos) at the 8 unit gives

```
┌Pmp—D-Tyr(Et)—                              ┐
            —Phe—Val—Asn—Cys—D-Arg—Gly(NH₂).
```

Substituting Boc-L-Phe(4-Me) for the amino acid at the 3 unit and Boc-Nle at the 4 unit in the synthesizer sequence reactions of Examples 1 and 2 gives

```
┌Pmp—D-Tyr(Et)—                              ┐
            —Phe(4-Me)—Nle—Asn—Cys—Arg—Gly(NH₂).
```

Substituting Boc-Abu for the amino acid at the 4-unit of Examples 1 and 2 gives

```
┌Pmp—D-Tyr(Et)—Phe—Abu—Asn—Cys—Arg—Gly(NH₂).┐
```

Substituting Boc-Cha at the 4 unit gives

```
┌Pmp—D-Tyr(Et)—Phe—Cha—Asn—Cys—Arg—Gly(NH₂).┐
```

Substituing Boc-D-Pba at the 2 unit and Boc-Chg at the 4 unit of the detailed reaction sequence of Examples 1 and 2 gives

```
┌Pmp—D-Pba—Phe—Chg—Asn—Cys—Arg—Gly(NH₂).┐
```

Substituting, in Examples 1 and 2, (Boc)-Lys at the 8 unit gives

```
┌Pmp—D-Tyr(Et)—Phe—Val—Asn—Cys—Lys—Gly—(NH₂).┐
```

Substituting β-(S-benzylmercapto-β-β-cyclotetramethylene)propionic acid for Pmp in Examples 1 and 2 gives the Tmp¹-D-Tyr(Et)² derivative.

EXAMPLE 6

Parenteral Dosage Unit Compositions:

A preparation which contains 0.5 mg of the cyclic octapeptide of Example 2 as a sterile dry powder for parenteral injection is prepared as follows: 0.5 mg of peptide amide is dissolved in 1 ml of an aqueous solution of 20 mg of mannitol. The solution is filtered under sterile conditions into a 2 ml ampoule and lyophilized. The powder is reconstituted before either intramuscular or intravenous injection to a subject suffering from edema susceptible to anti-ADH mechanism of action. The injection is repeated as necessary, from 1–5 times daily or in continuous i.v. drug injection. Other octapeptides of this invention are made up and used in like manner.

Nasal Dosage Unit Compositions:

340 mg of finely ground octapeptide of this invention such as the product of Example 2 is suspended in a mixture of 75 mg of benzyl alcohol and 1.395 g of a suspending agent such as a commercial mixture of semisynthetic glycerides of higher fatty acids. The suspension is placed in an aerosol 10 ml container which is closed with a metering valve and charged with aerosol propellants. The contents comprise 100 unit doses which are administered intranasally to an edematous subject from 1–6 times a day.

What is claimed is:

1. A polypeptide having the formula:

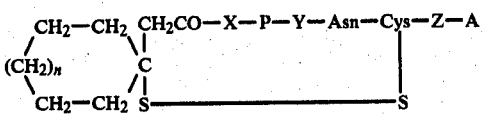

in which:
P is Phe or Phe(4'-Alk);
X is D-Phe, D-Val, D-Nva, D-Leu, D-Ile, D-Pba, D-Nle, D-Cha, D-Abu, D-Met, D-Chg, D or L-Tyr or D or L-Tyr(Alk);
Y is Val, Ile, Abu, Ala, Chg, Gln, Lys, Cha, Nle, Phe, Leu or Gly;
Z is D or L-Arg or D or L-Lys;
A is Gly(NH₂), Gly or Gly(NHAlk); and
n is 0–2, or pharmaceutically acceptable salts, esters or complexes thereof.

2. The compound of claim 1 in which P is Phe, X is D-Tyr(alk), n is 1 and Z is L-Arg and A is Gly(NH₂).

3. The compound of claim 1 having the formula:

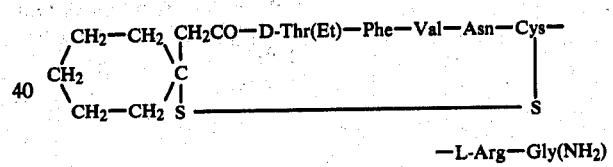

—L-Arg—Gly(NH₂)

4. The compound of claim 1 having the formula:

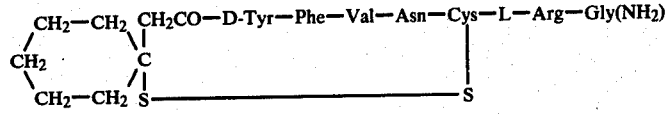

5. A pharmaceutical composition comprising a pharmaceutical carrier and, dispersed therein, a water diuretically effective but nontoxic quantity of a compound of claim 1.

6. The composition of claim 5 in which the compound has the formula:

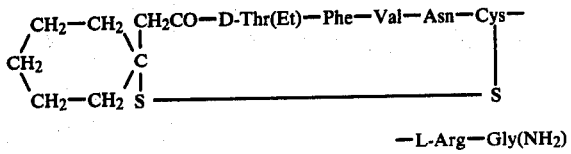

—L-Arg—Gly(NH₂)

7. The composition of claim 5 in which the compound has the formula:

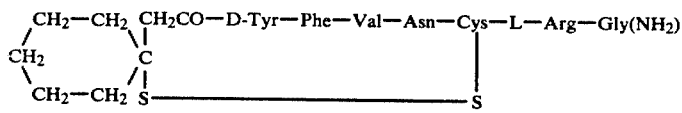

8. The composition of claim 5 in which the quantity of compound is selected from the range of 0.01–10 mg/kg.

9. The method of inducing a vasopressin antagonist effect in a patient in need of such an effect comprising administering internally to said patient a nontoxic, effective quantity therefor of a compound of claim 1.

10. The method of claim 9 in which the compound has the formula:

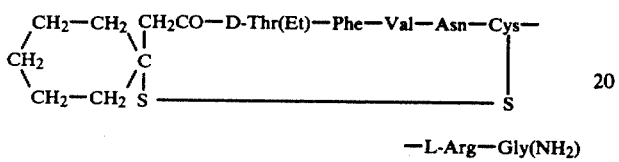

11. The method of claim 9 in which the compound has the formula:

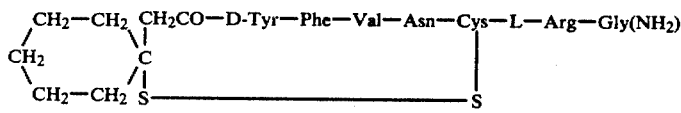

12. The method of claim 9 in which the quantity is selected from the range of 0.01–10 mg/kg which is administered from 1–5 times daily.

13. A polypeptide of the formula:

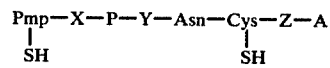

in which:
P is Phe or Phe(4′-Alk);
X is D-Phe, D-Val, D-Nva, D-Leu, D-Ile, D-Pba, D-Nle, D-Cha, D-Abu, D-Met, D-Chg, D or L-Tyr or D or L-Tyr(alk);
Y is Val, Ile, Abu, Ala, Chg, Gln, Lys, Cha, Nle, Phe, Leu or Gly;
Z is D or L-Arg, or D or L-Lys; and
A is Gly(NH₂), Gly or Gly(NH-Alk)

14. The compound of claim 13 being

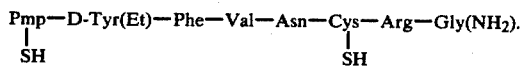

15. The compound of claim 13 being

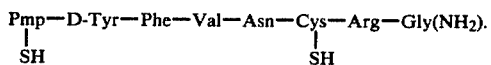

* * * * *

UNITED STATES PATENT AND TRADEMARK OFFICE
CERTIFICATE OF CORRECTION

PATENT NO. : 4,481,193
DATED : November 6, 1984
INVENTOR(S) : Fadia E. Ali and William F. Huffman It is certified that error appears in the above-identified patent and that said Letters Patent is hereby corrected as shown below:

Column 10, claim 3, line 38: "-D-Thr(Et)-" should read -D-Tyr(Et)- .

Column 10, claim 6, line 60: "-D-Thr(Et)-" should read -D-Tyr(Et)- .

Column 11, claim 10, line 18: "-D-Thr(Et)-" should read -D-Tyr(Et)- .

Signed and Sealed this

Second Day of April 1985

[SEAL]

Attest:

DONALD J. QUIGG

Attesting Officer    Acting Commissioner of Patents and Trademarks